T861029

DEFENSIVE PUBLICATION

UNITED STATES PATENT OFFICE

Published at the request of the applicant or owner in accordance with the Notice of Apr. 11, 1968, 849 O.G. 1221. Identification is by serial number of the application and the heading indicates the number of pages of specification, including claims, and of sheets of drawing contained in the application as originally filed. The file of this application is available to the public for inspection; reproduction may be purchased for 30 cents per sheet.

Applications published under the Defensive Publication Program have not been examined as to the merits of alleged invention. The Patent Office makes no assertion as to the novelty of the disclosed subject matter.

PUBLISHED APRIL 15, 1969

861 O.G. 704

707,405

PREPARATION OF PHTHALIC ACIDS BY SLOW OXIDATION

Frederic B. Kirby, 13 Council Trail, Indian Field, Del. 19703

Filed Feb. 23, 1968. Published Apr. 15, 1969

Class 260—524

No Drawing. 13 Pages Specification

High purity phthalic acids such as terephthalic acid are prepared from methyl-substituted benzenes such as p-xylene in solution in aliphatic monocarboxylic acid (e.g., acetic acid) in the presence of cobalt-containing catalyst (e.g., cobalt acetate tetrahydrate) and without the aid of a promoter, by contacting the reaction mixture, under essentially atmospheric pressure, with substantially pure molecular oxygen for a period of at least 5 days and preferably at least about 6.5 days, while agitating the reaction mixture and maintaining its temperature at about from 80 to 105° C., and preferably at least 90° C. The resulting phthalic acid is collected, e.g., by filtration, washed with aliphatic acid solvent (e.g., acetic acid), and then dried to give (based on the weight of initial methyl-substituted benzene) at least a 94% yield of phthalic acid (calculated as 100% acid) which acid has a purity of at least about 97% by weight.